Figure 1:
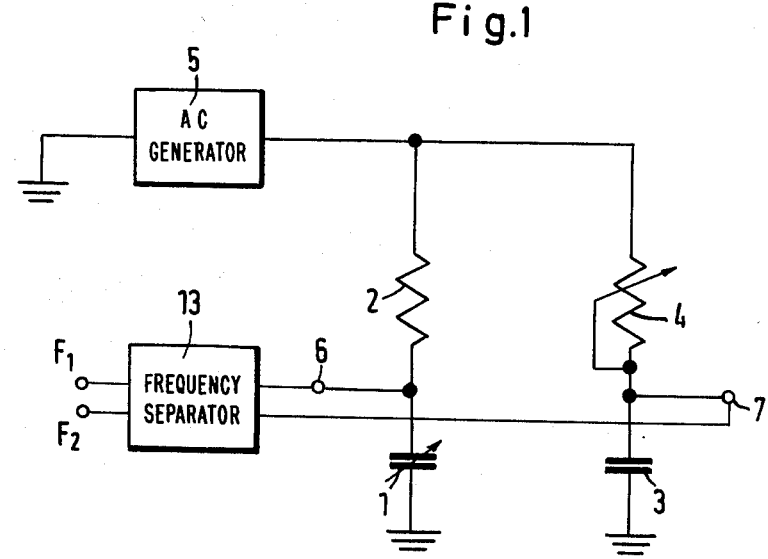

United States Patent [19]

Hennig et al.

[11] 4,296,754

[45] Oct. 27, 1981

[54] METHOD FOR DETERMINING THE VALUE OF CARDIOLOGIC QUANTITIES AND APPARATUS FOR PERFORMING SAID METHOD

[76] Inventors: Ewald M. C. Hennig, Ostendstrasse 62, D-6000 Frankfurt 1; Klaus Nicol, Adelheidstrasse 13, D-6000 Frankfurt 50, both of Fed. Rep. of Germany

[21] Appl. No.: 54,438

[22] Filed: Jul. 3, 1979

[30] Foreign Application Priority Data

Jul. 4, 1978 [DE] Fed. Rep. of Germany ....... 2829269

[51] Int. Cl.$^3$ .............................................. A61N 5/02
[52] U.S. Cl. .................................................. 128/694
[58] Field of Search ............... 128/668, 673, 675, 680, 128/681, 687, 689, 690, 691, 693, 694, 698, 722, 734, 774, 782

[56] References Cited

U.S. PATENT DOCUMENTS 2,834,338 5/1958 Carson .................................. 128/668
3,361,129 1/1968 Figar .................................... 128/694

OTHER PUBLICATIONS

Weed et al., "Medical and Biological Engineering", vol. 8, No. 1, Jan. 1970, pp. 59–70.

Primary Examiner—William E. Kamm
Attorney, Agent, or Firm—Lane, Aitken, Kice & Kananen

[57] ABSTRACT

The application concerns a method for determining the value of cardiologic quantities and an apparatus for performing such method.

In accordance with the invention capacities and capacity variations are measured in response to the electric properties of the body and its functional changes. The measurement is done by providing capacitive sensors. The capacitive sensors are each connected in a branch of a measuring bridge for capacity-voltage-transformation.

9 Claims, 5 Drawing Figures

METHOD FOR DETERMINING THE VALUE OF CARDIOLOGIC QUANTITIES AND APPARATUS FOR PERFORMING SAID METHOD

The invention relates to a method for determining the value of cardiologic quantities and apparatus for performing said method.

The invention relates to a method of determining the blood pressure, the flow of blood and value of other cardiologic quantities of human beings and animals.

Measuring of the blood pressure and the flow of blood are of special importance in medicine. Decisive data are obtainable by said measurements for the analysis of action of the heart and the blood supply of different parts of the human or animal body. Measuring of the blood flow allows a direct determination of the mechanical output of the heart, whereas the electrocardiology allows a substantially qualitative measurement of the heart action only by corresponding action currents.

Different methods of measuring the blood flow and apparatus for performing said methods are known (cf. H. Kresse: "Aspekte der Physik in der modernen Medizintechnik", a lecture held before the 51st meeting of physicists in Karlsruhe in 1977, and published in "Physikalische Blätter", 34th Year, No. 4/78).

For measuring the characteristic gas of the flow of blood, the blood volume ejected by the heart is determined by means of the blood flow through the lungs. By recording the oxygen absorption and measuring the oxygen percentage of mixed venous blood and arterial blood before and behind the lung the minute output of the heart can be determined.

This method leads to satisfactory results, but it is difficult to realize, since for the determination of the oxygen content of the mixed venous blood a central venous catheter must be introduced into the right chamber of the heart. This cannot be expected of the normal clinical routine.

According to the pigment dilution method, the time-dependent concentration gradient of the pigment which is responsive to the mixing process is measured by optical analysis at the ear after a colouring matter has been introduced into a vein. Besides the operation of the vascular system said method has the drawback that it is not continuous, that it cannot be repeated as often as required and gives only an average value.

The electromagnetic measuring of the blood flow is based on the fact that the ions in the blood are deflected by Lorentz forces within a magnetic field. The resulting potential difference is a measure for the blood flow. The stroke volume of each individual beating of the heart can be determined by said method, but it is disadvantageous that the artery or vein must be laid open operatively to allow the measurement. Furthermore, the signal can be deflected only when the magnetic field strength does not vary.

Measurings of blood flow can also be performed by means of ultrasonic echo sounding and by utilizing the Doppler effect of ultrasonic waves. In case of ultrasonic echo sounding the diameter of the heart chamber is measured by means of echo transmission times, and in case of assumed predetermined geometric forms of the heart chambers the stroke volume depends on the variation of the diameter. However, this measurement is affected with considerable errors up to 50%.

Measurings of blood flow are possible by measuring the velocity distribution in a vein by utilizing the ultrasonic Doppler effect. The drawbacks lie in the expensive technology which becomes necessary since the following conditions have to be fulfilled:

(a) The angle between the sound beam and the flow of blood must be measured.
(b) the cross-section averaged velocity must be calculated, and
(c) the cross section of the vein must be measured.

The impedance cardiography makes use of the fact that by the action of the heart the electric conductivity is varied with space and time by the flow of blood, and a measuring device was developed which detects the respective variations of resistance. The measuring device is provided with electrodes, of which two are applied at the neck and two are applied like a ring around the lower costal margin, and a low alternating current is applied, and the impedance is measured at the two inner electrodes of the two pairs of parallel electrodes by a voltage measurement. One is, however, very critical of this method, since the resistance of the body is also varied by displacement of organs and respiration.

The problem underlying the invention is to develop a simple method of determining the blood flow and value of other cardiologic quantities and a respective device, wherefor neither an operation of the body is necessary nor is it necessary to electrically contact the body.

According to the method of the invention this problem is solved therein that capacities and variations of capacities are detected by the provision of capacitive sensors at any place of the bodies of living beings in response to the electrical properties of the body and its changes conditioned by functions.

The solution according to the invention requires that the resilient blood-conveying vessels are expanded periodically by the increased pressure due to the beating of the heart and that thus the dielectric conditions and the capacity of a capacitor provided at the periphery of the body are varied. The capacity variation of the capacitive sensor or sensors is transformed by means of a capacity/voltage transducer into a voltage variation which can be made visible by simple means. In this way one can judge the pulse frequency, the blood pressure and the blood volume flowing through the vessels from the voltage variation.

The measuring effect is very clear for the following reason. The blood of a human being includes about 56% of blood plasma and about 44% of blood cells. The dielectric constant of the blood depends on the percentages and the dielectric constant of the individual blood constituents. The blood plasma includes up to 90% of water which is actually the main constituent of the blood. Due to the high dielectric constant of water of $\epsilon_r = 81$ the capacity variation is relatively large by the flow of blood.

It can be assumed that substantially only one variation of the magnitude of the vessels influences the capacity by the change of blood flow, since changes of the other dielectrics such as of the tissue, do either not occur or are negligibly small. An exception are parts of the bodies through which large substance-conveying channels run, such as the neck. Besides the cardiologic variables, the method according to the invention covers also the respiratory activity, since, due to the varying pressure conditions in the thoracic cavity caused by the respiration, the blood pressure is slightly decreased during inhaling and slightly increased during exhaling. As the respiration frequency is considerably lower than the pulse frequency it is possible, by an electronic filter at the output of the capacity/voltage transducer, to measure the respiration frequency only.

An apparatus for performing the method is characterized in that the capacitive sensor or sensors for capacity/voltage transformation are connected in a branch of each measuring bridge.

Further developments of the method according to the invention and of the apparatus for performing said method are characterized by the subclaims.

The method according to the invention has the advantage that the body of which the value of a cardiologic quantity is to be detected does not have to be contacted directly. Moreover, the values of cardiologic quantities can be measured at different parts of the body since the capacitive sensors may be applied to any point of the body. The apparatus provided to perform the method according to the invention has by far a simpler construction than e.g. that one used for impedance cardiography, and moreover, the measured values are especially easy to evaluate since they are output signals of a bridge which are directly an indication for the flow of the blood.

One embodiment of the apparatus according to the invention as well as of an especially suited capacitive sensor and the measured results obtainable by said apparatus will be described hereinafter by the drawings.

Figure 2:
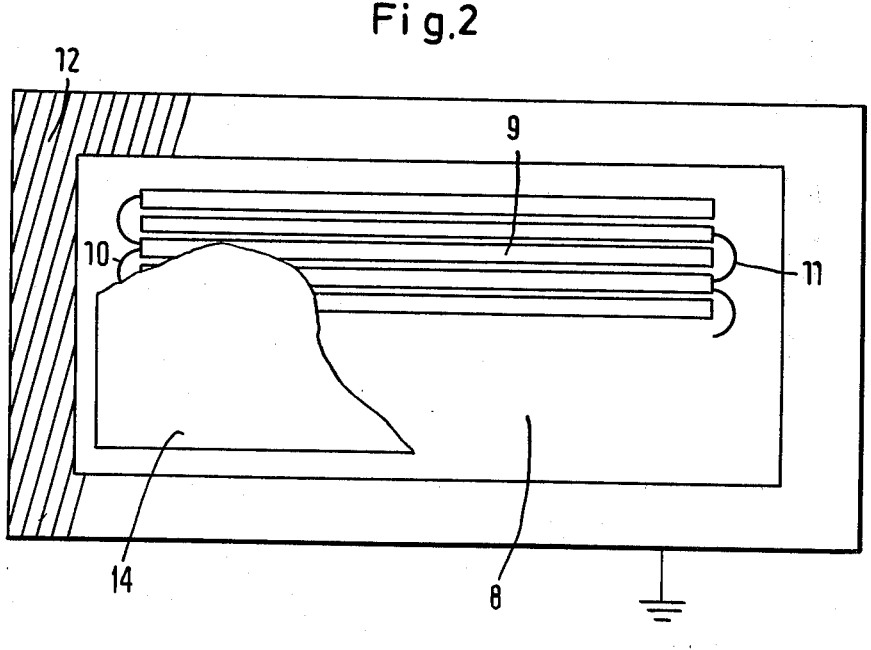
Figure 3:
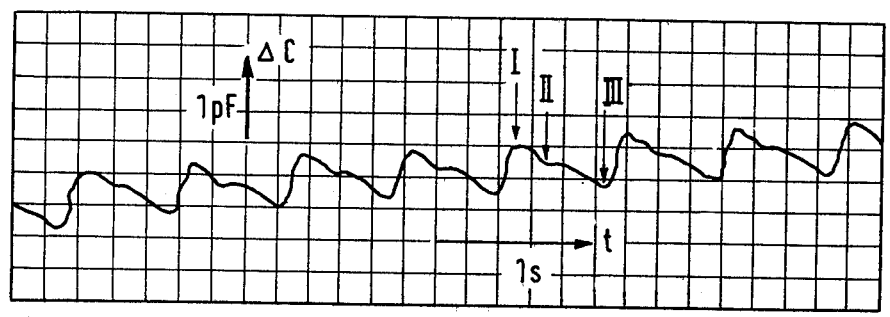
Figure 4:
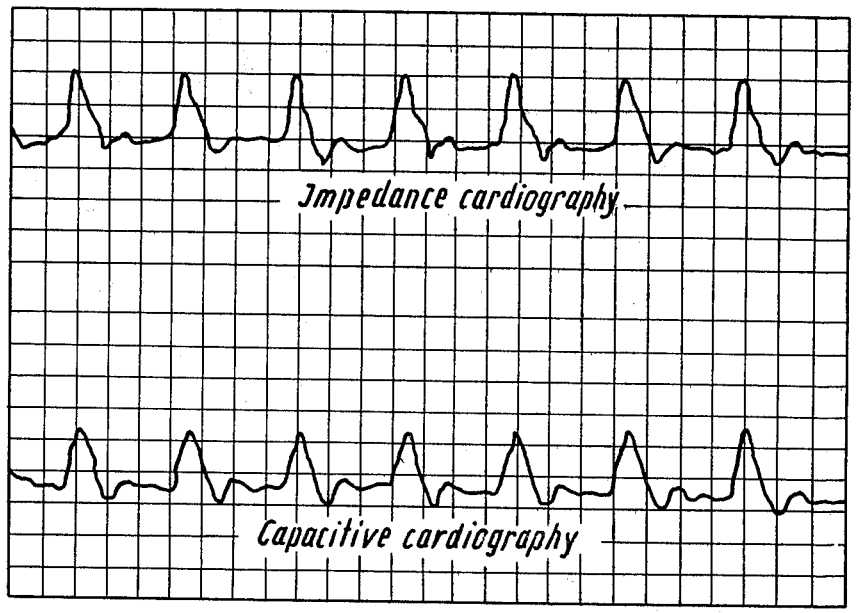
Figure 5:
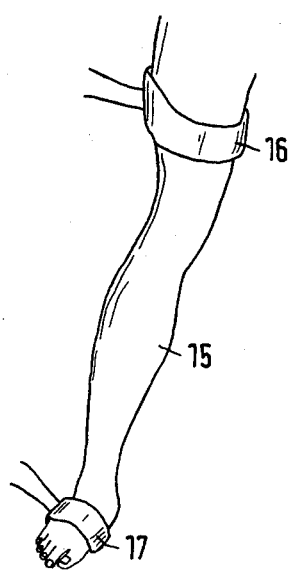

FIG. 1 illustrates a measuring bridge with a capacitive sensor for capacity-voltage transformation, FIG. 2 illustrates an embodiment of a capacitive sensor, FIG. 3 shows a measuring curve taken with a bridge according to FIG. 1, FIG. 4 illustrates a signal measured in accordance with the method of the invention in comparison with a signal quantity measured by impedance cardiography, and FIG. 5 shows the use of two sensors on the leg of a human being.

FIG. 1 illustrates an embodiment of the bridge. The bridge comprises a branch wherein a capacitor 1 is provided as a capacitive sensor, wherein furthermore an ohmic resistance 2 is provided. It comprises a second branch including a capacitor 3 of a constant capacity, and a variable resistor 4. Both capacitors are grounded. At the connecting point between the two branches and the two resistors 2 and 4, respectively, a signal is fed in by a generator 5.

A terminal 6 is provided between the capacitive sensor 1 and the resistor 2, and a terminal 7 is provided between the capacitor 3 and the variable resistor 4. When an AC-signal is supplied to the bridge by the generator 5, a signal appears at terminal 6 according to the voltage divider of capacitor 1 and resistor 2, and a signal appears at terminal 7 according to the voltage divider of capacitor 3 and resistor 4. Thus, the voltage difference between terminals 6 and 7 indicates the change of the capacity of the capacitor 1. In accordance with the changes of the capacitor 1 at two different frequencies (pulse frequency and respiration frequency) the voltage difference signal between the terminals 6 and 7 is composed of two signals of different frequency. The terminals 6 and 7 are connected to a circuit 13 separating signals of different frequencies. This circuit has two output leads F1, F2 for the two signals of different frequency. At the output lead F1 the signal of the pulse frequency is appearing, and at the output lead F2 the signal with the respiration frequency is appearing.

Hereinafter follows a description of an embodiment of a capacitive sensor as it is suited for many purposes. A plurality of parallel electrically conductive strips 9 are provided on a non-conducting foil 8. Every other strip is electrically interconnected so that one group of the interconnected strips defines a capacitor plate 10 and the second group of the interconnected strips defines a second capacitor plate 11. The whole system is isolated by a non-conducting foil 14 from the body to be measured in order to exclude electrical conducting. The width of this foil may vary to a large extent so that a random distance between the conducting strips and the body can be provided. Also, there may be a distance between the outer surface of the foil 14 and the surface of the body. On the side of the system averted from the body an electrically conductive film 12 is provided in isolated form and grounded to exclude capacity variations caused by outer influences. The whole arrangement forms a collar which is placed like a ring around the part of the body to be measured.

The capacitor plates are connected to the other circuit elements of the measuring bridge by shielded lines. The measuring bridge has a resolution of $(\Delta C/C) < 10^{-6}$ and can detect absolute capacity variations of less than $10^{-3}$ pF. At the output of the measuring bridge a voltage signal is available which is proportional to the capacity variation of the sensor.

The measurements performed by the measuring bridge according to the invention are illustrated in the diagrams of FIGS. 3 and 4. The collar with the capacitive sensor was put around a man's neck. The diagram of FIG. 3 illustrates a time-controlled measurement of the blood volume by direct measurement of the capacity variation. The displacement of the signal level depends on the respiration. "I" designates the highest systolic blood pressure. After the steep leading edge to the peak of the pulse at "I", follows a slow trailing edge with a clear recess at "II" due to the closing of the aortic valves. At "III" the lowest diastolic blood pressure can be seen.

The diagram of FIG. 4 shows a comparison of the blood flow measurement by impedance cardiography with that by a capacitive measurement according to the method of the invention. As in the impedance cardiography a differential signal dz/dt is present, also the output signal of the bridge was differentiated for comparison. The diagrams show a clear coincidence of both methods. At the beginning of the systole the current intensity increases rapidly, reaches a maximum and drops less rapidly. At the end of the systole it passes zero. After the end of the systole, the curve characteristic is negative for a short time due to the closing of the aortic valves, which is caused by a returning blood flow shortly before the complete closing of the aortic valves. Reference is made to the book by Meyer-Warden, K. "Einführung in die biologische und medizinische Messtechnik", Stuttgart 1975.

FIG. 5 shows a leg 15 of a human being. A sensor 16 is attached to the upper leg and a sensor 17 is attached to the foot. By comparing the signals of sensors 16 and 17 in amplitude or phase, the change of blood flow in the leg can be investigated. This can be done by visual comparison.

We claim:
1. A method for determining the value of cardiologic quantities comprising:
encircling a portion of a body having a blood-conveying vessel with capacitor plates of a capacitor, so that the body portion engages the capacitor and defines the dielectric of the capacitor;

maintaining the capacitor plates fixed relative to one another; and measuring changes in the capacitance of the capacitor.

2. The method of claim 1 wherein the step of measuring includes:

providing a bridge having two branches and including said capacitor in one of said branches;

sending a signal through the branches; and measuring the potential difference between the two branches.

3. The method of claim 2 wherein the step of measuring the potential difference includes:

separating the potential difference into different frequencies; and measuring the potential difference at each frequency.

4. The method of claim 1 wherein the step of measuring includes measuring changes in the dielectric of the capacitor.

5. The method of claim 4 wherein the step of measuring includes measuring changes in the geometric dimensions of the dielectric.

6. Apparatus for determining the value of cardiologic quantities comprising:

a capacitive measuring bridge circuit having a plurality of branches;

means for transmitting a signal through the branches;

means for measuring the potential difference between each of branches; and a capacitor in one of said branches for encircling a portion of a body having a blood-conveying vessel, the capacitor defining a collar which includes a plurality of parallel, electrically conductive strips isolated within a non-conducting material, the conductive strips comprising a pair of capacitor plates.

7. The apparatus of claim 6 wherein the collar is conformable to various portions of the body.

8. The apparatus of claim 6, wherein the means for measuring includes a circuit separating signals of different frequencies.

9. The apparatus of claim 6, further including shielded connections between the capacitor plates and the capacitive measuring bridge circuit.

* * * * *